(12) United States Patent
Friedlander et al.

(10) Patent No.: US 8,560,365 B2
(45) Date of Patent: Oct. 15, 2013

(54) PROBABILISTIC OPTIMIZATION OF RESOURCE DISCOVERY, RESERVATION AND ASSIGNMENT

(75) Inventors: Robert R. Friedlander, Southbury, CT (US); James R. Kraemer, Santa Fe, NM (US); Robin Lougee-Heimer, Yorktown Heights, NY (US); Kirill M. Osipov, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 422 days.

(21) Appl. No.: 12/795,847

(22) Filed: Jun. 8, 2010

(65) Prior Publication Data
US 2011/0301967 A1 Dec. 8, 2011

(51) Int. Cl.
*G06Q 10/00* (2012.01)

(52) U.S. Cl.
USPC ...................................................... 705/7.12

(58) Field of Classification Search
USPC ............... 706/46, 50; 709/223; 705/8, 14, 45, 705/7.12
See application file for complete search history.

(56) References Cited

U.S. PATENT DOCUMENTS

| | | | |
|---|---|---|---|
| 4,890,227 A | 12/1989 | Watanabe et al. | |
| 5,070,453 A | 12/1991 | Duffany | |
| 5,111,391 A | 5/1992 | Fields et al. | |
| 5,128,871 A | 7/1992 | Schmitz | |
| 5,148,365 A | 9/1992 | Dembo | |
| 5,216,593 A | 6/1993 | Dietrich et al. | |
| 5,764,740 A | 6/1998 | Holender | |
| 5,838,918 A | 11/1998 | Prager et al. | |
| 5,880,598 A | 3/1999 | Duong | |
| 6,021,403 A | 2/2000 | Horvitz et al. | |
| 6,049,776 A | 4/2000 | Donnelly et al. | |
| 6,076,166 A | 6/2000 | Moshfeghi et al. | |
| 6,102,856 A | 8/2000 | Groff et al. | |
| 6,164,975 A | 12/2000 | Weingarden et al. | |
| 6,212,524 B1 | 4/2001 | Weissman et al. | |
| 6,272,483 B1 | 8/2001 | Joslin et al. | |
| 6,289,340 B1 | 9/2001 | Puram et al. | |
| 6,321,207 B1 | 11/2001 | Ye | |
| 6,449,641 B1 | 9/2002 | Moiin et al. | |
| 6,484,155 B1 | 11/2002 | Kiss et al. | |
| 6,578,068 B1 | 6/2003 | Bowman-Amuah | |
| 6,604,160 B1 | 8/2003 | Le et al. | |
| 6,647,374 B2 | 11/2003 | Kansal | |
| 6,675,159 B1 | 1/2004 | Lin et al. | |
| 6,905,816 B2 | 6/2005 | Jacobs et al. | |
| 6,937,147 B2 | 8/2005 | Dilbeck et al. | |
| 6,954,736 B2 | 10/2005 | Menninger et al. | |
| 7,181,428 B2 | 2/2007 | Lawrence | |

(Continued)

OTHER PUBLICATIONS

U.S. Appl. No. 12/851,995—Specification Filed Aug. 6, 2010.

(Continued)

*Primary Examiner* — Gerald J. O'Connor
*Assistant Examiner* — Natalie A Pass
(74) *Attorney, Agent, or Firm* — John R. Pivnichny; Law Office of Jim Boice (57) ABSTRACT

A computer implemented method, system and/or computer program product allocate multiple resources from multiple organizations. A series of requests for multiple resources from multiple organizations is received. The multiple resources are required to accomplish a specific task, and each of the multiple resources is assigned a probability of consumption. Probabilities of availability of the multiple resources are then determined and transmitted to the organizations.

15 Claims, 3 Drawing Sheets

(56) References Cited

U.S. PATENT DOCUMENTS

| | | | |
|---|---|---|---|
| 7,213,009 B2 | 5/2007 | Pestotnik et al. | |
| 7,295,925 B2 | 11/2007 | Breed et al. | |
| 7,343,316 B2 | 3/2008 | Goto et al. | |
| 7,400,257 B2 | 7/2008 | Rivas | |
| 7,403,922 B1 | 7/2008 | Lewis et al. | |
| 7,457,764 B1 | 11/2008 | Bullock et al. | |
| 7,460,019 B2 | 12/2008 | Henderson | |
| 7,464,147 B1 | 12/2008 | Fakhouri et al. | |
| 7,516,142 B2 | 4/2009 | Friedlander et al. | |
| 7,523,118 B2 | 4/2009 | Friedlander et al. | |
| 7,539,623 B1 | 5/2009 | Wyatt | |
| 7,558,745 B2 | 7/2009 | Cullen et al. | |
| 7,584,160 B2 | 9/2009 | Friedlander et al. | |
| 7,630,948 B2 | 12/2009 | Friedlander et al. | |
| 7,630,986 B1 | 12/2009 | Herz et al. | |
| 7,647,288 B2 | 1/2010 | Friedlander et al. | |
| 7,693,736 B1 | 4/2010 | Chu et al. | |
| 7,702,605 B2 | 4/2010 | Friedlander et al. | |
| 7,739,606 B2 | 6/2010 | Sawada et al. | |
| 7,752,154 B2 | 7/2010 | Friedlander et al. | |
| 7,801,885 B1 | 9/2010 | Verma | |
| 7,930,262 B2 | 4/2011 | Friedlander et al. | |
| 7,933,228 B2 | 4/2011 | Coley | |
| 8,001,008 B2 | 8/2011 | Engle | |
| 8,010,516 B2 | 8/2011 | Ishii et al. | |
| 8,055,603 B2 | 11/2011 | Angell et al. | |
| 8,204,779 B1 | 6/2012 | Hughes et al. | |
| 2001/0034632 A1 | 10/2001 | Wilkinson | |
| 2002/0019764 A1 | 2/2002 | Mascarenhas | |
| 2002/0052756 A1 | 5/2002 | Lomangino | |
| 2002/0059201 A1 | 5/2002 | Work | |
| 2002/0107824 A1 | 8/2002 | Ahmed et al. | |
| 2002/0111922 A1 | 8/2002 | Young et al. | |
| 2002/0115447 A1 | 8/2002 | Martin et al. | |
| 2002/0182573 A1 | 12/2002 | Watson | |
| 2003/0033180 A1 | 2/2003 | Shekar et al. | |
| 2003/0065544 A1 | 4/2003 | Elzinga et al. | |
| 2003/0088491 A1 | 5/2003 | Liu et al. | |
| 2003/0097291 A1 | 5/2003 | Freedman | |
| 2003/0140063 A1 | 7/2003 | Pizzorno et al. | |
| 2003/0177038 A1 | 9/2003 | Rao | |
| 2003/0220830 A1 | 11/2003 | Myr | |
| 2003/0220860 A1 | 11/2003 | Heytens et al. | |
| 2004/0006694 A1 | 1/2004 | Heelan et al. | |
| 2004/0122787 A1* | 6/2004 | Avinash et al. | 706/50 |
| 2004/0243422 A1 | 12/2004 | Weber et al. | |
| 2004/0267595 A1 | 12/2004 | Woodings et al. | |
| 2005/0004823 A1 | 1/2005 | Hnatio | |
| 2005/0004828 A1 | 1/2005 | deSilva et al. | |
| 2005/0038608 A1 | 2/2005 | Chandra et al. | |
| 2005/0080806 A1 | 4/2005 | Doganata et al. | |
| 2005/0101873 A1 | 5/2005 | Misczynski et al. | |
| 2005/0144062 A1 | 6/2005 | Mittal et al. | |
| 2005/0149466 A1 | 7/2005 | Hale et al. | |
| 2005/0165594 A1 | 7/2005 | Chandra et al. | |
| 2005/0198486 A1 | 9/2005 | Desmond et al. | |
| 2005/0222989 A1 | 10/2005 | Haveliwala et al. | |
| 2005/0240668 A1* | 10/2005 | Rolia et al. | 709/223 |
| 2006/0010090 A1 | 1/2006 | Brockway et al. | |
| 2006/0031110 A1 | 2/2006 | Benbassat et al. | |
| 2006/0036560 A1 | 2/2006 | Fogel | |
| 2006/0069514 A1 | 3/2006 | Chow et al. | |
| 2006/0105830 A1 | 5/2006 | Nemitz et al. | |
| 2006/0155627 A1 | 7/2006 | Horowitz | |
| 2006/0184412 A1 | 8/2006 | Kagan et al. | |
| 2006/0194186 A1 | 8/2006 | Nanda | |
| 2006/0200435 A1 | 9/2006 | Flinn et al. | |
| 2006/0218010 A1 | 9/2006 | Michon et al. | |
| 2006/0226991 A1 | 10/2006 | Rivas | |
| 2006/0294085 A1 | 12/2006 | Rose et al. | |
| 2007/0073654 A1 | 3/2007 | Chow et al. | |
| 2007/0073754 A1 | 3/2007 | Friedlander et al. | |
| 2007/0073799 A1 | 3/2007 | Adjali et al. | |
| 2007/0112735 A1 | 5/2007 | Holloway et al. | |
| 2007/0150325 A1 | 6/2007 | Bjornson | |
| 2007/0168307 A1 | 7/2007 | Floudas et al. | |
| 2007/0174090 A1 | 7/2007 | Friedlander et al. | |
| 2007/0174091 A1 | 7/2007 | Friedlander et al. | |
| 2007/0174101 A1 | 7/2007 | Li et al. | |
| 2007/0179356 A1 | 8/2007 | Wessel | |
| 2007/0185737 A1 | 8/2007 | Friedlander et al. | |
| 2007/0203872 A1 | 8/2007 | Flinn et al. | |
| 2007/0244701 A1 | 10/2007 | Erlanger et al. | |
| 2007/0274337 A1 | 11/2007 | Purpura | |
| 2008/0015871 A1 | 1/2008 | Eder | |
| 2008/0028409 A1* | 1/2008 | Cherkasova et al. | 718/104 |
| 2008/0065576 A1 | 3/2008 | Friedlander et al. | |
| 2008/0077463 A1 | 3/2008 | Friedlander et al. | |
| 2008/0082356 A1 | 4/2008 | Friedlander et al. | |
| 2008/0082374 A1 | 4/2008 | Kennis et al. | |
| 2008/0147694 A1 | 6/2008 | Ernest et al. | |
| 2008/0155104 A1 | 6/2008 | Quinn et al. | |
| 2008/0167929 A1 | 7/2008 | Cao et al. | |
| 2008/0172352 A1* | 7/2008 | Friedlander et al. | 706/46 |
| 2008/0177687 A1 | 7/2008 | Friedlander et al. | |
| 2008/0177688 A1 | 7/2008 | Friedlander et al. | |
| 2008/0189402 A1* | 8/2008 | Betzler et al. | 709/223 |
| 2008/0208801 A1 | 8/2008 | Friedlander et al. | |
| 2008/0208813 A1 | 8/2008 | Friedlander et al. | |
| 2008/0208814 A1 | 8/2008 | Friedlander et al. | |
| 2008/0208832 A1 | 8/2008 | Friedlander et al. | |
| 2008/0208838 A1 | 8/2008 | Friedlander et al. | |
| 2008/0208875 A1 | 8/2008 | Friedlander et al. | |
| 2008/0208901 A1 | 8/2008 | Friedlander et al. | |
| 2008/0208902 A1 | 8/2008 | Friedlander et al. | |
| 2008/0208903 A1 | 8/2008 | Friedlander et al. | |
| 2008/0208904 A1 | 8/2008 | Friedlander et al. | |
| 2008/0209493 A1 | 8/2008 | Choi et al. | |
| 2008/0246629 A1 | 10/2008 | Tsui et al. | |
| 2008/0281974 A1 | 11/2008 | Slothouber et al. | |
| 2008/0288862 A1 | 11/2008 | Smetters et al. | |
| 2008/0294459 A1 | 11/2008 | Angell et al. | |
| 2008/0294692 A1 | 11/2008 | Angell et al. | |
| 2009/0024553 A1 | 1/2009 | Angell et al. | |
| 2009/0106179 A1 | 4/2009 | Friedlander et al. | |
| 2009/0112670 A1 | 4/2009 | Black et al. | |
| 2009/0138300 A1 | 5/2009 | Kagan et al. | |
| 2009/0198733 A1 | 8/2009 | Gounares et al. | |
| 2009/0287503 A1 | 11/2009 | Angell et al. | |
| 2009/0287674 A1 | 11/2009 | Bouillet et al. | |
| 2009/0287683 A1 | 11/2009 | Bennett | |
| 2009/0299766 A1 | 12/2009 | Friedlander et al. | |
| 2009/0299928 A1 | 12/2009 | Kongtcheu | |
| 2010/0010832 A1 | 1/2010 | Boute et al. | |
| 2010/0042456 A1* | 2/2010 | Stinchcombe et al. | 705/8 |
| 2010/0063877 A1* | 3/2010 | Soroca et al. | 705/14.45 |
| 2010/0077438 A1 | 3/2010 | Ansari | |
| 2010/0131028 A1 | 5/2010 | Hsu et al. | |
| 2010/0191516 A1 | 7/2010 | Benish et al. | |
| 2010/0223581 A1 | 9/2010 | Manolescu et al. | |
| 2010/0228715 A1 | 9/2010 | Lawrence | |
| 2011/0054968 A1 | 3/2011 | Galaviz | |
| 2011/0093287 A1 | 4/2011 | Dicks et al. | |
| 2011/0275907 A1 | 11/2011 | Inciardi et al. | |
| 2012/0108984 A1 | 5/2012 | Bennett et al. | |

OTHER PUBLICATIONS

U.S. Appl. No. 12/903,376—Specification Filed Oct. 13, 2010.

U.S. Appl. No. 12/875,261—Specification Filed Sep. 3, 2010.

T. Vercauteren et al., "Hierarchical Forecasting of Web Server Workload Using Sequential Monte Carlo Training", IEEE Transactions on Signal Processing, vol. 55, No. 4, pp. 1286-1297, Apr. 2007.

K. Vanthournout et al., "A Taxonomy for Resource Discovery", Pers Ubiquit Comput 9, pp. 81-89, 2005.

C. Srisuwanrat et al., "Optimal Scheduling of Probabilistic Repetitive Projects Using Completed Unit and Genetic Algorithms", Proceedings of the 2007 Winter Simulation Conference, pp. 2151-2158, 2007.

S. Bharathi et al., "Scheduling Data-Intensive Workflows on Storage Constrained Resources", Works 09, Portland, OR, pp. 1-10 Nov. 15, 2009.

J. Redondo et al., "Solving the Multiple Competitive Facilities Location and Design Problem on the Plane", Massachusetts Institute of (56) References Cited

OTHER PUBLICATIONS

Technology, Evolutionary Computation, vol. 17, No. 1, pp. 21-53, 2009.
H. Van et al., "Autonomic Virtual Resource Management for Service Hosting Platforms", Cloud'09, pp. 1-8, May 23, 2009.
U.S. Appl. No. 12/903,376—Non-Final Office Action Mailed Jul. 30, 2012.
U.S. Appl. No. 12/875,261—Notice of Allowance Mailed Sep. 27, 2012.
Phillip E. Hayes et al., "Picking Up the Pieces: Utilizing Disaster Recovery Project Management to Improve Readiness and Response Time," IEEE Industry Applications Magazine, Nov./Dec. 2002, pp. 1-10 (Abstract).
Kun Wang et al., "A Mathematical Approach to Disaster Recovery Planning," Proceedings of the First International Conference on Semantics, Knowledge, and Grid, 2005, pp. 1-3 (Abstract).
E. A. Silver, "An Overview of Heuristic Solution Methods," The Journal of the Operational Research Society, vol. 55, No. 9, Sep. 2004, pp. 936-956 (Abstract).
Smith et al., "Collaborative Approaches to Research," HEFCE Fundamental Review of Research Policy and Planning, Final Report, Apr. 2000, pp. 1-117.
William E. Souder, "Analytical Effectiveness of Mathematical Models for R&D Project Selection," Management Science, vol. 19, No. 8, Application Seires, Apr. 1973, pp. 907-923 (Abstract).
J. Altmann et al., "Cooperative Software Development: Concepts, Model and Tools," Technology of Object-Oriented Languages and Systems, 1999, pp. 1-14.
Shou-Qi Cao et al., "Research on Resource Scheduling for Development Process of Complicated Product," Computer Supported Cooperative Work in Design, 2005. Proceedings of the Ninth International Conference on, vol. 1, pp. 229-233 (Abstract).
Ming Chen et al., "Research on Organization Method of Development Activities for Complicated Product," Computer Supported Cooperative Work in Design, 2005. Proceedings of the Ninth International Conference on, vol. 1, pp. 234-239 (Abstract).
Luckham et al., "Event Processing Glossary," Jul. 2008, pp. 1-19. http://complexevents.com.
Dept of Health and Human Services Agency for Healthcare Research and Quality, "AHRQ Quality Indicators—Patient Safety Indicators—Technical Specifications," 2012, pp. 1-149. http://www.qualityindicators.ahrq.gov.
Wong et al., "Rule-Based Anomaly Pattern Detection for Detecting Disease Outbreaks," AAAI-02 Proceedings, 2002, pp. 1-7.
Schadow et al., "Discussion Paper: Privacy-Preserving Distributed Queries for a Clinical Case Research Network," IEE International Conference on Data Mining Workshop on Privacy, Security, and Data Mining, 2002 (Abstract).
U.S. Appl. No. 12/851,995—Non-Final Office Action Mailed Apr. 25, 2012.
U.S. Appl. No. 12/884,665—Specification Filed Sep. 17, 2010.
U.S. Appl. No. 12/875,261—Non-Final Office Action Mailed Feb. 14, 2012.
U.S. Appl. No. 12/884,665—Non-Final Office Action Mailed Apr. 11, 2012.
U.S. Appl. No. 13/253,431—Specification Filed Oct. 5, 2011.
U.S. Appl. No. 13/253,431—Non-Final Office Action Mailed Nov. 10, 2011.
U.S. Appl. No. 12/884,665—Final Office Action Mailed Oct. 18, 2012.
U.S. Appl. No. 12/903,376—Notice of Allowance Mailed Dec. 19, 2012.
U.S. Appl. No. 12/851,995—Final Office Action Mailed Nov. 8, 2012.
U.S. Appl. No. 13/253,431—Non-Final Office Action Mailed Jan. 3, 2013.
Grzymala-Busse, "Knowledge Acquisition Under Uncertainty—A Rough Set Approach," Journal of Intelligent and Robotic Systems, 1988, vol. 1, Issue 1, pp. 3-16 (Abstract).
P. Palazzari et al., "Synthesis of Pipelined Systems for the Contemporaneous Execution of Periodic and Aperiodic Tasks With Hard Real-Time Constraints", 18th International Parallel and Distributed Processing Symposium, 121. IEEE Comput. Soc, Los Alamitos, CA, USA, 2004, pp. LVI-289 (Abstract Only).
RL Dillon et al., "Optimal Use of Budget Reserves to Minimize Technical and Management Failure Risks During Complex Project Development", IEEE Transactions on Engineering Management, vol. 52, No. 3, pp. 382-395, Aug. 2005 (Abstract Only).
U.S. Appl. No. 12/851,995—Examiner's Answer Mailed May 10, 2013.
U.S. Appl. No. 12/851,995—Supplemental Examiner's Answer Mailed May 22, 2013.
U.S. Appl. No. 12/884,6656—Examiner's Answer Mailed May 16, 2013.
U.S. Appl. No. 13/253,431—Final Office Action Mailed May 21, 2013.

* cited by examiner

PROBABILISTIC OPTIMIZATION OF RESOURCE DISCOVERY, RESERVATION AND ASSIGNMENT

BACKGROUND

The present disclosure relates to the field of computers, and specifically to the use of computers in allocating resources. Still more particularly, the present disclosure relates to the use of computers to allocate resources to multiple business entities.

BRIEF SUMMARY

A computer implemented method, system and/or computer program product allocate multiple resources from multiple organizations. A series of requests for multiple resources from multiple organizations is received. The multiple resources are required to accomplish a specific task, and each of the multiple resources is assigned a probability of consumption. Probabilities of availability of the multiple resources are then determined and transmitted to the organizations.

DETAILED DESCRIPTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
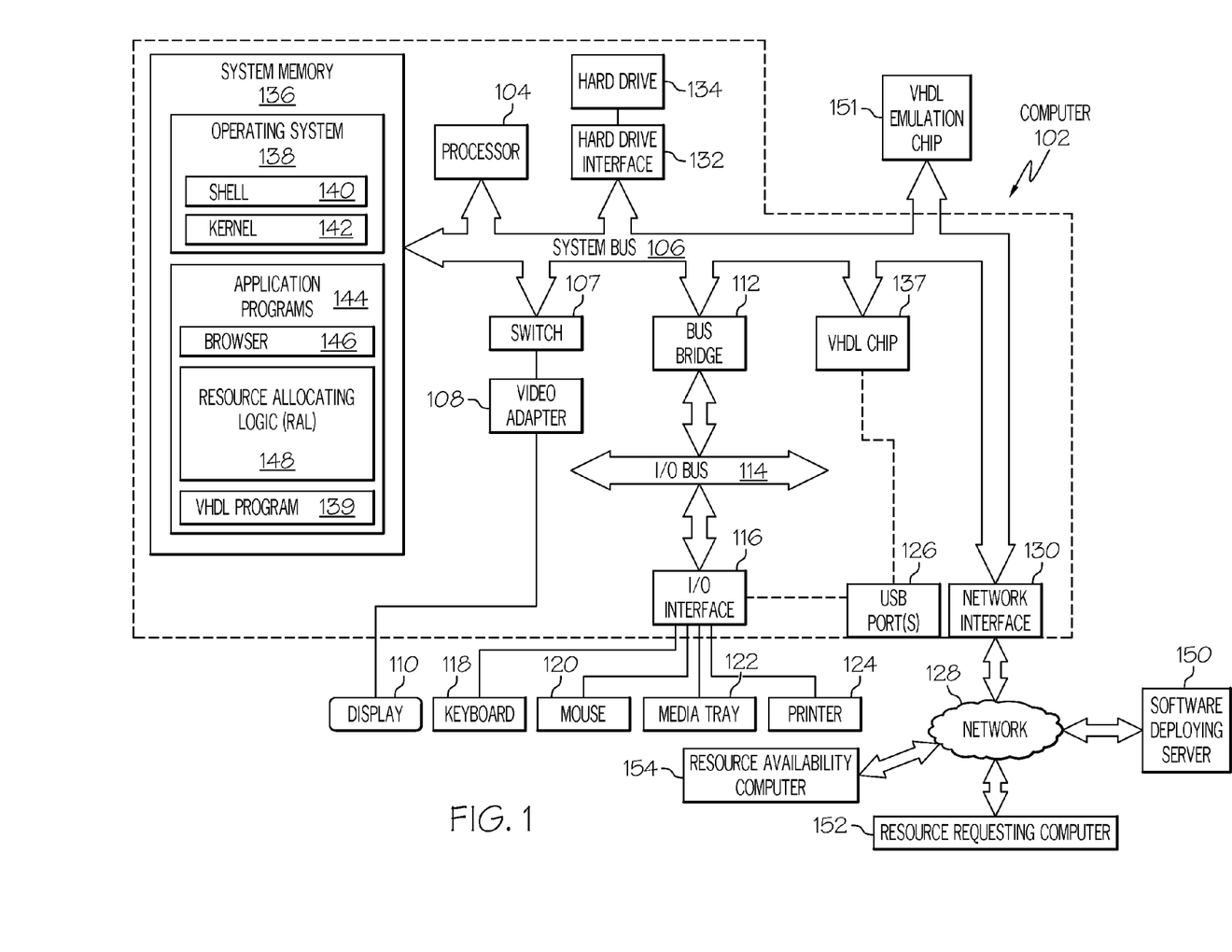
FIG. 1 depicts an exemplary computer in which the present disclosure may be implemented.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, resource requesting computer 152 and/or resource availability computer 154.

Computer 102 includes a processor 104 that is coupled to a system bus 106. Processor 104 may utilize one or more processors, each of which has one or more processor cores. A video adapter 108, which drives/supports a display 110, is also coupled to system bus 106. In one embodiment, a switch 107 couples the video adapter 108 to the system bus 106. Alternatively, the switch 107 may couple the video adapter 108 to the display 110. In either embodiment, the switch 107 is a switch, which may be mechanical, that allows the display 110 to be coupled to the system bus 106, and thus to be functional only upon execution of instructions (e.g., resource allocating logic—RAL 148 described below) that support the processes described herein.

System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and (if a VHDL chip 137 is not utilized in a manner described below), external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other described computer systems.

Application programs 144 in computer 102's system memory (as well as software deploying server 150's system memory) also include a resource allocating logic (RAL) 148. RAL 148 includes code for implementing the processes described below, including those described in FIGS. 2-3. In one embodiment, computer 102 is able to download RAL 148 from software deploying server 150, including in an on-demand basis, wherein the code in RAL 148 is not downloaded until needed for execution to define and/or implement the improved enterprise architecture described herein. Note further that, in one embodiment of the present invention, software deploying server 150 performs all of the functions associated with the present invention (including execution of RAL 148), thus freeing computer 102 from having to use its own internal computing resources to execute RAL 148.

Also stored in system memory 136 is a VHDL (VHSIC hardware description language) program 139. VHDL is an exemplary design-entry language for field programmable gate arrays (FPGAs), application specific integrated circuits (ASICs), and other similar electronic devices. In one embodiment, execution of instructions from RAL 148 causes VHDL program 139 to configure VHDL chip 137, which may be an FPGA, ASIC, etc.

In another embodiment of the present invention, execution of instructions from RAL 148 results in a utilization of VHDL program 139 to program a VHDL emulation chip 151. VHDL emulation chip 151 may incorporate a similar architecture as described above for VHDL chip 137. Once RAL 148 and VHDL program 139 program VHDL emulation chip 151, VHDL emulation chip 151 performs, as hardware, some or all functions described by one or more executions of some or all of the instructions found in RAL 148. That is, the VHDL emulation chip 151 is a hardware emulation of some or all of the software instructions found in RAL 148. In one embodiment, VHDL emulation chip 151 is a programmable read only memory (PROM) that, once burned in accordance with instructions from RAL 148 and VHDL program 139, is permanently transformed into a new circuitry that performs the functions needed to perform the process described below in FIGS. 2-3.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
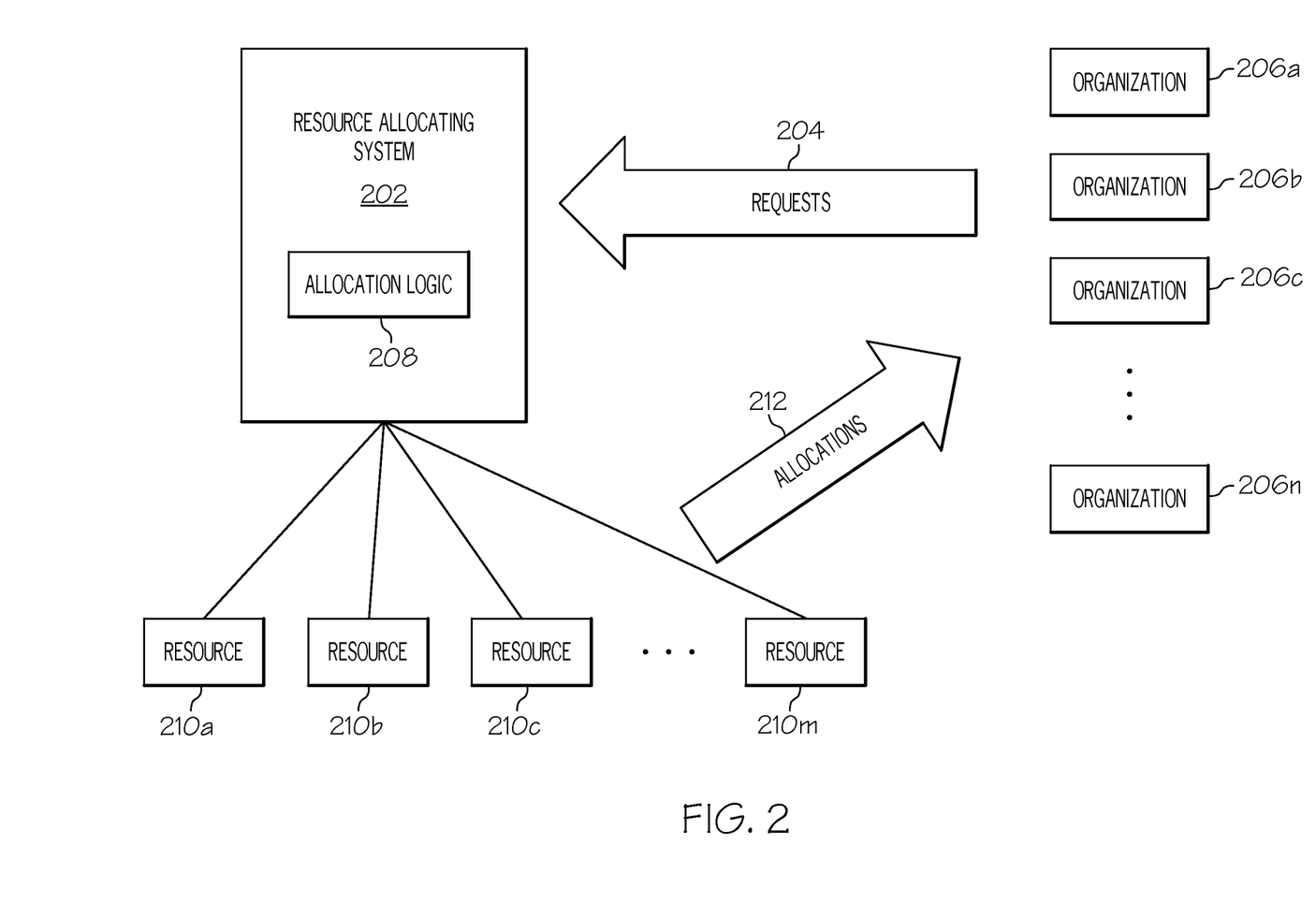
FIG. 2 illustrates relationships among a resource allocating system, multiple organizations, and multiple resources.

Referring now to FIG. 2, a relationship among a resource allocating system 202, multiple organizations 206a-n (where "n" is an integer), and multiple resources 210a-m (where "m" is an integer) is presented. In one embodiment, resource allocating system 202 can be some or all of computer 102 shown in FIG. 1. Organizations 206a-n can communicate with resource allocating system 202 via a resource requesting computer, such as resource requesting computer 152 shown in FIG. 1. The existence of resources 210a-m, or even the resources 210a-m themselves, can be made known by a resource computer such as resource availability computer 154 shown in FIG. 1. As depicted, resource allocating system 202 utilizes allocation logic 208 (e.g., RAL 148 shown in FIG. 1) to receive requests 204 for resources from organizations 206a-n. In a manner described herein, these requests 204 may ultimately result in resource allocations 212, which allocations are also under the control and direction of allocation logic 208.

Figure 3:
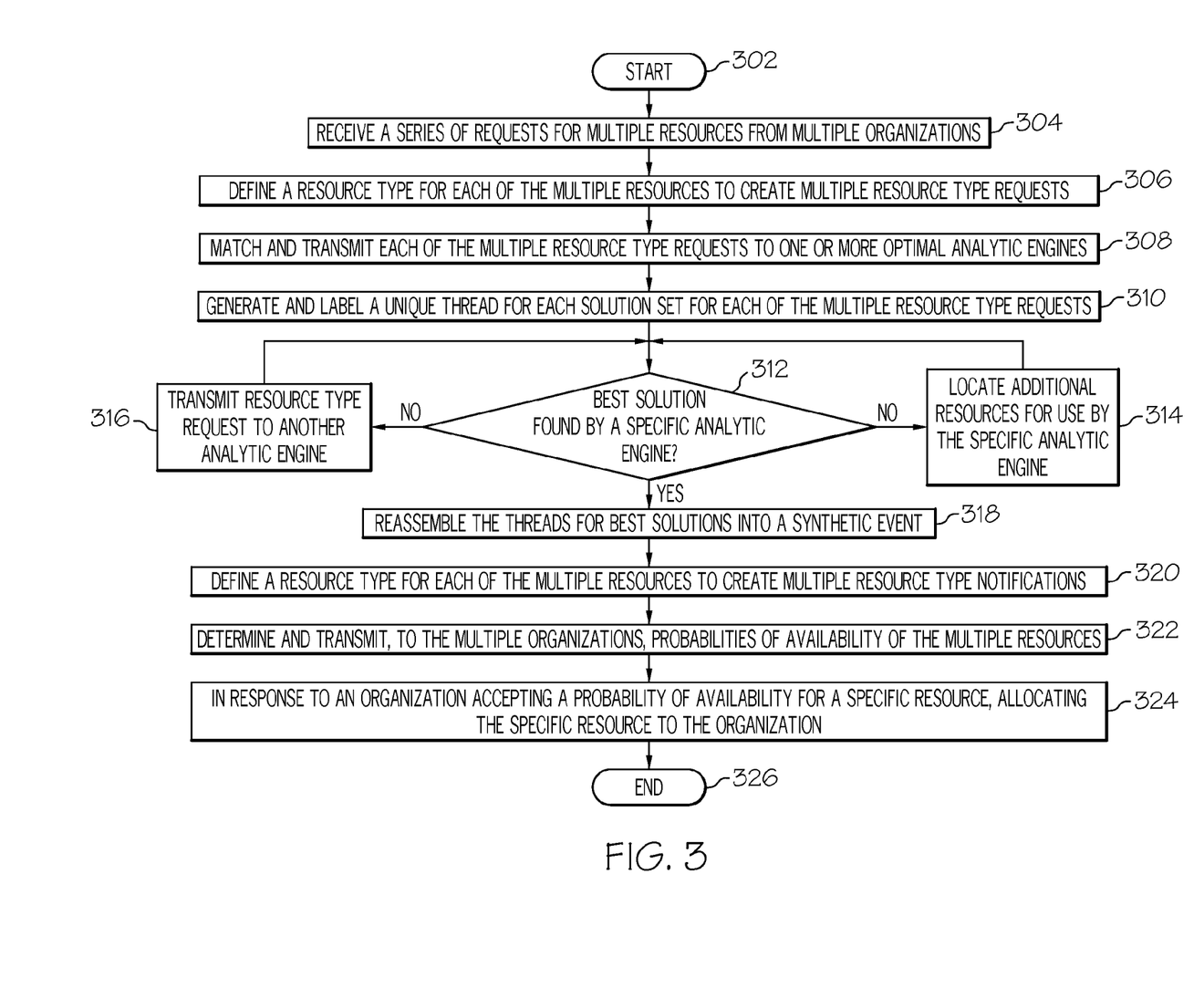
FIG. 3 is a high level flow chart of one or more exemplary steps taken by a processor to allocate multiple resources from multiple organizations.

With reference now to FIG. 3, a high level flow chart of steps taken to allocate resources is presented. After initiator block 302, a series of requests for multiple resources are received from multiple organizations (block 304). These multiple resources are required to accomplish a specific task. In one embodiment, this task is a medical research project, and the requisite resources are tissue samples, hardware research equipment (e.g., magnetic resonance imaging—MRI equipment), computer time for processing data on a computer, cloud, etc. In one embodiment, the task may be any task that requires personnel with specific qualifications, based on their educational background, known interests, past writings, work experience, social media, etc. related to the task at hand. In one embodiment, the task is the treatment of a group of medical patients, and the resources include health care workers, treatment rooms/equipment, hospital beds, etc. The requisite resources can also include funding from grants, endowments, enterprise budgets, etc.

As depicted in block 306, a resource type is defined for each of the multiple resources to create multiple resource type requests. Thus, each time an organization/enterprise requests a resource, these requests will be in resource-specific formats. Thus, if the request is for personnel, then the request will contain a flag or similar indicator letting the resource allocating system know that personnel, not hardware or other resources, are needed. Similarly, if the organization requests material such as tissue for medical research, then the resource allocating system will detect a tag in the request so indicating. As depicted in block 308, by matching these tags/flags/indicators from the resource request, the resource request can be matched to a specific analytic engine. Analytic engines are logic that match requests to specific resources based on the resource availability, any constraints on the resources (i.e., does the requesting organization have the proper environment to support the resource, such as hardware to run certain types of software, storage facilities to store tissue samples, funds to pay personnel, etc.), whether the organization has used the requested resource in the past (thus indicating that the request is "serious" rather than speculative), etc. In one embodiment, each different analytic engine uses a different analytic technique to produce one or more solution sets for locating and apportioning resources needed to satisfy a best solution to each of the multiple resource type requests. A best solution is a solution that is deemed to comply with predefined parameters (i.e., rules for the organization, legal requirements, etc.) and constraints (described herein) for that resource and the requesting organization.

As described in block 310, a unique thread for each solution set for each of the multiple resource type requests is generated and labeled. This thread is a software thread that is executed by allocation logic (e.g., allocation logic 208) within the resource allocating system. By creating a unique thread for each of the solution sets created by the analytic engines, the system allows solutions to be spawned off during the middle of optimization of the overall solution set, thus permitting fine granularity for updating/improving the solutions. As depicted in query block 312, a determination is made as to whether the best solution (i.e., allocating the proper resource in response to the resource request from the enterprise/organization) has been found by a specific analytic engine. If not then there are two options. As described in block 314, one option is to locate additional resources for use by the specific analytic engine. In this option, the assumption is made that the analytic engine used to match the request with the optimal resource is the right engine, but it simply has not been afforded access to the right resources. As described in block 316, another option is to transmit the resource type request to another analytic engine. In this option, the assumption is that the logic within the first analytic engine simply does not have the ability to match the request with the proper resource, and thus another analytic engine is needed. In one embodiment, the optimal analytic engine is matched (determined) based on a probability of the task being performed. Thus, one analytic engine may have access to a large array of resources, since those resources have dealt with that analytic engine in the past, and know that there is a high probability that the resources will ultimately be allocated to the requesting organization. For example, assume that the organization includes a Nobel laureate, who always gets whatever she wants from the organization and resource community. Requests from this organization would be directed to a "high probability" analytic engine, which would have access to many resources. However, a resource request from a lower-tier requester, such as one who has a history of not receiving applied-for grants, or simply has no history at all, would be directed to send her requests to a "low probability" analytic engine, which would have access to fewer resources (or to higher-priced resources).

As described in block 318, once the best solution to the resource request is found, the threads for the best solutions to the multiple resource type requests are reassembled into a synthetic event. This synthetic event, which is an emulation of the task and the task's completion using the allocated resources, matches a description of the task to which the resources will be allocated, and maintains a probabilistic, time period sensitive inventory of resources, requests, and demand likelihood of fulfilling the multiple resource type requests. Thus, the synthetic event describes which resources will be allocated, when they will be allocated, and the likelihood that they in fact will be allocated to the specific task/organization. A resource type is defined for each of the multiple resources to create multiple resource type notifications (block 320). Thus, each resource type has a unique notification type (marked by tags/flags). As each of the multiple resources has now been assigned a probability of consumption, these probabilities are then transmitted as part of the unique notification types to the multiple organizations that have requested the resources (block 322). It is then incumbent on the requester to accept whatever probability of availability has been assigned for a specific set of resources. If the requester accepts this probability of availability, then the resource set is allocated to (i.e., reserved for and/or transmitted to) the requester (block 324). The process ends at terminator block 326.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer implemented method of allocating multiple resources, the computer implemented method comprising:

a processor receiving a series of requests for multiple resources from multiple organizations, wherein the multiple resources are required to accomplish a task, and wherein each of the multiple resources has been assigned a probability of consumption, wherein the probability of consumption is based on a resource acquisition authorization history of a person who is requesting the multiple resources, wherein a first person having a first resource acquisition authorization history of always receiving approval for acquiring requested resources has a higher probability of consumption than a second person having a second resource acquisition authorization history of never receiving approval for acquiring requested resources;

the processor determining and transmitting, to the multiple organizations, probabilities of availability of the multiple resources;

defining a resource type for each of the multiple resources to create multiple resource type requests;

matching and transmitting each of the multiple resource type requests to one or more optimal analytic engines, wherein each different optimal analytic engine uses a different analytic technique to produce one or more solution sets for locating and apportioning resources needed to satisfy a best solution to each of the multiple resource type requests, wherein the best solution complies with predefined parameters;

generating and labeling a unique thread for each solution set for each of the multiple resource type requests; and reassembling threads for best solutions, to the multiple resource requests, into a synthetic event, wherein the synthetic event is an emulation of the task and a completion of the task to which the multiple resources are allocated, wherein the synthetic event matches a description of the task, and wherein the synthetic event maintains a probabilistic, time period sensitive inventory of resources, requests, and demand likelihood of fulfilling the multiple resource type requests, wherein the synthetic event describes which particular resources will be allocated to the task, when said particular resources will be allocated to the task, and a likelihood of said particular resources being allocated to the task; and in response to a specific analytic engine failing to produce the best solution, transmitting a specific resource type request to another analytic engine.

2. The computer implemented method of claim 1, further comprising:

in response to an organization accepting a probability of availability for a specific resource, allocating the specific resource to a customer.

3. The computer implemented method of claim 1, further comprising:

in response to a specific analytic engine failing to produce the best solution, locating additional resources for use by the specific analytic engine.

4. The computer implemented method of claim 1, wherein said each different optimal analytic engine is matched based on a probability of the task being performed.

5. The computer implemented method of claim 1, further comprising:

defining a resource type for each of the multiple resources to create multiple resource type notifications, wherein the multiple resource type notifications are used to transmit a series of notifications of availabilities of the multiple resources.

6. The computer implemented method of claim 1, wherein each of the multiple resources comprises multiple hierarchies of sub-resources that are required to accomplish the task.

7. The computer implemented method of claim 1, wherein the multiple resources comprise funding from grants, and wherein the probability of consumption is further based on whether a particular organization has historically used funding from grants.

8. The computer implemented method of claim 7, further comprising:
  determining if a particular person has the specialized skills based on past writing, work experience and education of said particular person.

9. The computer implemented method of claim 1, wherein the task is a medical research project, and wherein the multiple resources comprise tissue samples required for the medical research.

10. The computer implemented method of claim 1, wherein the task is medical treatment of a group of patients, and wherein the multiple resources comprise health care providers.

11. The computer implemented method of claim 1, wherein the task is a medical research project, and wherein the multiple resources comprise hardware research equipment.

12. A computer program product for allocating multiple resources, the computer program product comprising:
  a non-transitory computer readable storage media;
  first program instructions to receive a series of requests for multiple resources from multiple organizations, wherein each of the multiple resources has been assigned a probability of consumption, and wherein each of the multiple resources comprises multiple hierarchies of sub-resources that are required to accomplish a task;
  second program instructions to determine and transmit, to the multiple organizations, probabilities of availability of the multiple resources;
  third program instructions to define a resource type for each of the multiple resources to create multiple resource type requests;
  fourth program instructions to match and transmit each of the multiple resource type requests to one or more optimal analytic engines, wherein each different optimal analytic engine uses a different analytic technique to produce one or more solution sets for locating and apportioning resources needed to satisfy a best solution to each of the multiple resource type requests, wherein the best solution complies with predefined parameters;
  fifth program instructions to generate and label a unique thread for each solution set for each of the multiple resource type requests;
  sixth program instructions to reassemble threads for best solutions to the multiple resource type requests into a synthetic event, wherein the synthetic event matches a description of the task and maintains a probabilistic, time period sensitive inventory of resources, requests, and demand likelihood of fulfilling the multiple resource type requests; and
  seventh program instructions to, in response to a specific analytic engine failing to produce the best solution, transmit a specific resource type request to another analytic engine; and wherein
  the first, second, third, fourth, fifth, sixth, and seventh program instructions are stored on the non-transitory computer readable storage media.

13. The computer program product of claim 12, further comprising:
  eighth program instructions to, in response to as specific analytic engine failing to produce the best solution, locate additional resources for use by the specific analytic engine, wherein the eighth program instructions are stored on the non-transitory computer readable storage media.

14. A computer system comprising:
  a central processing unit (CPU), a computer readable memory, and a computer readable storage media;
  first program instructions to receive a series of requests for multiple resources from multiple organizations, wherein each of the multiple resources has been assigned a probability of consumption, and wherein each of the multiple resources comprises multiple hierarchies of sub-resources that are required to accomplish a task;
  second program instructions to determine and transmit, to the multiple organizations, probabilities of availability of the multiple resources;
  third program instructions to define a resource type for each of the multiple resources to create multiple resource type requests;
  fourth program instructions to match and transmit each of the multiple resource type requests to one or more optimal analytic engines, wherein each different optimal analytic engine uses a different analytic technique to produce one or more solution sets for locating and apportioning resources needed to satisfy a best solution to each of the multiple resource type requests, wherein the best solution complies with predefined parameters;
  fifth program instructions to generate and label a unique thread for each solution set for each of the multiple resource type requests;
  sixth program instructions to reassemble threads for best solutions to the multiple resource type requests into a synthetic event, wherein the synthetic event matches a description of the task and maintains a probabilistic, time period sensitive inventory of resources, requests, and demand likelihood of fulfilling the multiple resource type requests; and
  seventh program instructions to, in response to a specific analytic engine failing to produce the best solution, transmit a specific resource type request to another analytic engine; and wherein
  the first, second, third, fourth, fifth, sixth, and seventh program instructions are stored on the non-transitory computer readable storage media for execution by the CPU via the computer readable memory.

15. The computer system of claim 14, further comprising:
  eighth program instructions to define a resource type for each of the multiple resources to create multiple resource type notifications, wherein the multiple resource type notifications are used to transmit the series of notifications of availabilities of the multiple resources, and wherein the eighth program instructions are stored on the computer readable storage media for execution by the CPU via the computer readable memory.

* * * * *